United States Patent
Echigo et al.

(10) Patent No.: US 7,006,344 B2
(45) Date of Patent: Feb. 28, 2006

(54) CAPACITOR COMPRISING BIS(4-MERCAPTOPHENYL) SULFIDE DERIVATIVE

(75) Inventors: Noriyasu Echigo, Hyogo (JP); Kazuyoshi Honda, Osaka (JP); Yoshiaki Kai, Osaka (JP); Masaru Odagiri, Hyogo (JP); Hisaaki Tachihara, Shimane (JP); Hideki Matsuda, Tottori (JP); Jun Katsube, Shimane (JP); Kazuo Iwaoka, Shimane (JP); Takanori Sugimoto, Shimane (JP); Nobuki Sunagare, Shimane (JP)

(73) Assignee: Matsushita Electric Industrial Co., Ltd., Kadoma (JP)

( * ) Notice: Subject to any disclaimer, the term of this patent is extended or adjusted under 35 U.S.C. 154(b) by 18 days.

(21) Appl. No.: 10/332,548

(22) PCT Filed: Jul. 23, 2001

(86) PCT No.: PCT/JP01/06315

§ 371 (c)(1),
(2), (4) Date: Apr. 11, 2003

(87) PCT Pub. No.: WO02/08180

PCT Pub. Date: Jan. 31, 2002

(65) Prior Publication Data

US 2003/0189808 A1 Oct. 9, 2003

(51) Int. Cl.
*H01G 4/14* (2006.01)

(52) U.S. Cl. ............... 361/311; 361/524; 526/286; 526/289

(58) Field of Classification Search ........ 528/373–388; 526/286, 289, 321, 323.1; 361/311, 524
See application file for complete search history.

(56) References Cited

U.S. PATENT DOCUMENTS

| | | | | |
|---|---|---|---|---|
| 2,636,022 A | * | 4/1953 | Brooks et al. ............... | 526/289 |
| 4,046,744 A | | 9/1977 | Jenkins | |
| 5,013,823 A | * | 5/1991 | Mizuno et al. ............. | 528/388 |
| 5,125,138 A | | 6/1992 | Shaw et al. | |
| 5,736,616 A | | 4/1998 | Ching et al. | |
| 6,206,550 B1 | * | 3/2001 | Fukushima et al. ......... | 362/335 |
| 6,541,591 B1 | * | 4/2003 | Olson et al. ................ | 526/284 |

FOREIGN PATENT DOCUMENTS

| | | |
|---|---|---|
| EP | 0 147 696 | 7/1985 |
| JP | 57-187327 | 11/1982 |
| JP | 63-31929 | 8/1985 |
| JP | 61272917- | * 3/1986 |
| JP | 2-247212 | 10/1990 |
| JP | 2-258819 | 10/1990 |
| JP | 6-151652 | 5/1994 |
| JP | 6-291346 | 10/1994 |
| JP | 8-157320 | 6/1996 |
| JP | 10-71667 | 3/1998 |
| JP | 10-151676 | 6/1998 |
| JP | 10-309770 | 11/1998 |
| JP | 11-147272 | 6/1999 |
| JP | 11-322897 | 11/1999 |
| JP | 2000-218738 | 8/2000 |
| JP | 2000-338667 | 12/2000 |
| JP | 2001-64363 | 3/2001 |
| JP | 2001-64364 | 3/2001 |
| JP | 2001310911 A | * 11/2001 |
| JP | 2002-20508 | 1/2002 |
| JP | 2002-37770 | 2/2002 |

* cited by examiner

*Primary Examiner*—Marc S. Zimmer
(74) *Attorney, Agent, or Firm*—Hamre, Schumann, Mueller & Larson, P.C.

(57) ABSTRACT

The present invention provides a bis(4-mercaptophenyl) sulfide derivative represented by general formula 1. This derivative is a monomer that can form a dielectric film suitable for an electronic component. The present invention further provides a method for producing this derivative and an electronic component having high characteristics under excellent humidity and high temperature.

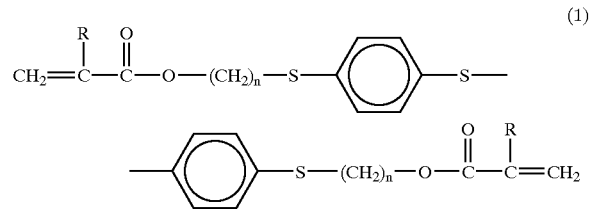

16 Claims, 6 Drawing Sheets

CAPACITOR COMPRISING BIS(4-MERCAPTOPHENYL) SULFIDE DERIVATIVE

TECHNICAL FIELD

The present invention relates to bis(4-mercaptophenyl) sulfide derivatives and a method for producing the same, and an electronic component.

BACKGROUND ART

Conventionally, a resin film has been used for a dielectric film in a capacitor or the like. Such a dielectric film is formed by irradiating a monomer deposited in a substrate with electron beams or ultraviolet rays to polymerize the monomer, as disclosed in JP 63-32929 B, JP 11-147272 A, and U.S. Pat. No. 5,125,138. As the monomer used for forming dielectric films, for example, dimethylol tricyclodecane diacrylate and 1,9-nonanediol diacrylate or the like have been used.

However, electronic components using the dielectric films formed of the above-described monomers have a problem in that the characteristics are not sufficient. In particular, electronic components using the dielectric films formed of the above-described monomers have the problem that the characteristics are not sufficient under high humidity and high temperature.

In order to solve the problem, it is an object of the present invention to provide a monomer that can provide dielectric films suitable for electronic components and a method for producing the same, and an electronic component having excellent characteristics under high humidity and high temperature.

DISCLOSURE OF INVENTION

As a result of in-depth research to achieve the above object, the inventors of the present invention found a novel monomer. To be specific, the monomer of the present invention is a bis(4-mercaptophenyl) sulfide derivative represented by general formula 1 below.

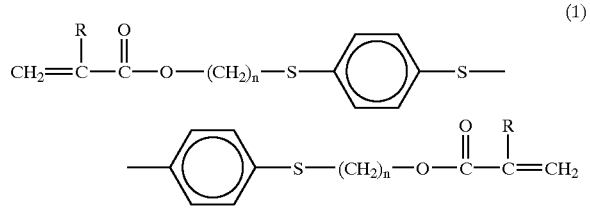

wherein R is hydrogen or a methyl group, and n is an integer of 1 to 4.

The bis(4-mercaptophenyl) sulfide derivative of the present invention is preferable as a monomer for forming a dielectric film used in an electronic component.

In the bis(4-mercaptophenyl) sulfide derivative of the present invention, R may be hydrogen and n may be 2. This embodiment can provide a particularly preferable monomer for forming a dielectric film used in an electronic component.

Furthermore, a method of the present invention for producing a bis(4-mercaptophenyl) sulfide derivative includes a first step of reacting bis(4-mercaptophenyl) sulfide represented by chemical formula 2 below with ω-haloalkyl alcohol having not more than 4 carbon atoms, thereby producing an organic compound represented by general formula 3 below, and a second step of reacting alkyl ester acrylate or alkyl ester methacrylate with the organic compound represented by general formula 3, thereby producing a bis(4-mercaptophenyl) sulfide derivative of general formula 1 below.

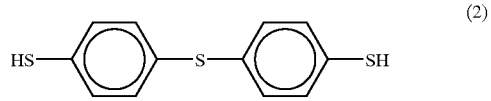

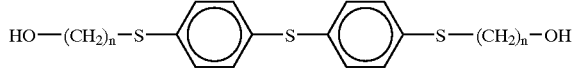

wherein n is an integer of 1 to 4.

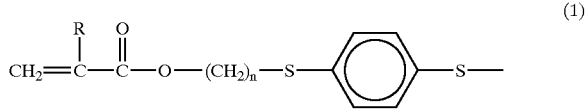

wherein R is hydrogen or a methyl group, and n is an integer of 1 to 4.

According to the method of the present invention for producing a bis(4-mercaptophenyl) sulfide derivative, the monomer represented by general formula 1 can be produced easily.

In the method of the present invention, the ω-haloalkyl alcohol may be 2-haloethanol in the first step, and methyl acrylate may be reacted with the compound represented by general formula 3 in the second step. According to this embodiment, the bis(4-mercaptophenyl) sulfide derivative that is particularly preferable as a monomer for forming a dielectric film used in an electronic component can be produced easily.

In the method of the present invention, the first step may be performed in the presence of alkali metal carbonate, which is a base catalyst. Furthermore, the second step may be performed in the presence of alkoxy titanium or an organotin compound, which is a catalyst for transesterification. According to this embodiment, the bis(4-mercaptophenyl) sulfide derivative can be produced efficiently.

Furthermore, an electronic component of the present invention is provided with a dielectric film, wherein the dielectric film is formed by forming a thin film containing at least one type of monomer and polymerizing the monomer in the thin film, and the monomer has a molecular structure in which sulfur and an aromatic ring are covalently bonded or a molecular structure in which sulfur and an aromatic ring are bonded via an alkylene group. According to the electronic component of the present invention, an electronic component having satisfactory characteristics under high humidity and high temperature can be obtained.

The electronic component of the present invention further may include a pair of electrodes opposed to each other with at least a part of the dielectric film interposed therebetween. This embodiment can provide an electronic component, such as a capacitor, having excellent characteristics even under high humidity and high temperature.

In the electronic component of the present invention, it is preferable that the monomer includes one or a plurality of monomers represented by general formulae 1 and 4, and chemical formulae 5 and 6.

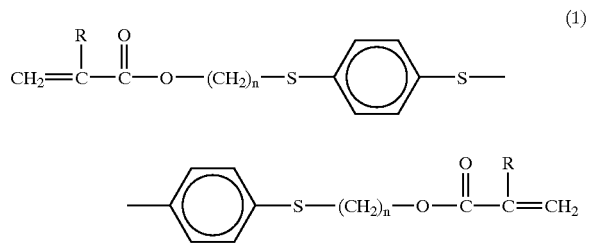
(1)

wherein R is hydrogen or a methyl group, and n is an integer of 1 to 4.

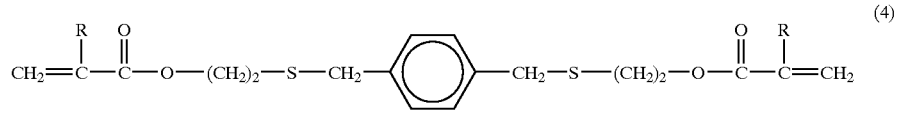
(4)

wherein R is hydrogen or a methyl group.

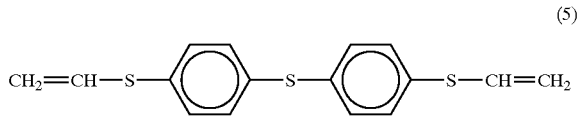
(5)

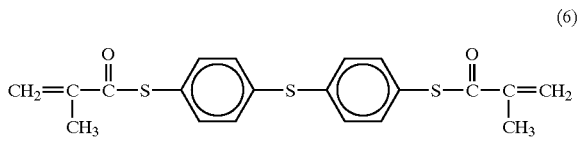
(6)

This embodiment can provide an electronic component having particularly excellent characteristics under high humidity and high temperature.

In the electronic component of the present invention, the thin film further may include an additive. As the additive, for example, an antioxidant can be used. This embodiment can prevent oxidation of the dielectric film.

BEST MODE FOR CARRYING OUT THE INVENTION

Figure 1A:
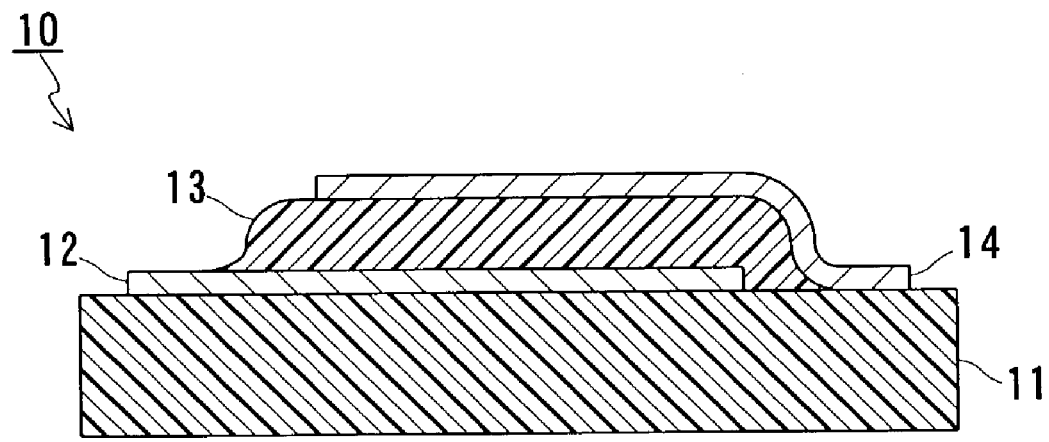
FIG. 1A is a cross-sectional view showing an example of a capacitor, which is an electronic component of the present invention.

Hereinafter, embodiments of the present invention will be described with reference to the accompanying drawings. In the following description, the same elements bear the same reference numeral and duplicate description may be omitted.

Embodiment 1

In Embodiment 1, bis(4-mercaptophenyl) sulfide derivatives of the present invention will be described.

The bis(4-mercaptophenyl) sulfide derivatives of the present invention are represented by general formula 1 below.

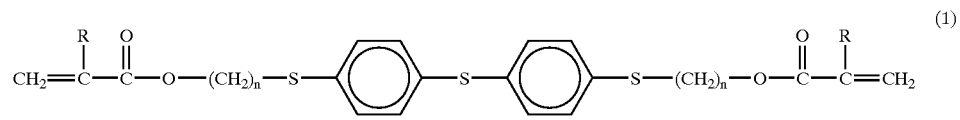
(1)

wherein R is hydrogen or a methyl group, and n is an integer of 1 to 4.

The bis(4-mercaptophenyl) sulfide derivatives represented by general formula 1 can be produced by the method described in Embodiment 2.

The bis(4-mercaptophenyl) sulfide derivatives represented by general formula 1 can be used as a monomer for forming dielectric films (resin films used in electronic components. When forming a dielectric film using this monomer, first, a thin film containing this monomer is formed, and the thin film is irradiated with electron beams or ultraviolet rays. Using this monomer, dielectric films suitable for electronic components can be formed. In particular, when the monomer of a bis(4-mercaptophenyl) sulfide derivative having hydrogen as R and 2 as n in general formula 1 is used to form dielectric films for capacitors, the capacitors have excellent characteristics even under high humidity and high temperature.

According to another aspect, the present invention relates to utilization of an organic compound represented by general formula 1 as a monomer of a resin.

Embodiment 2

In Embodiment 2, a method for producing the bis(4-mercaptophenyl) sulfide derivatives represented by general formula 1 described in Embodiment 1 will de described.

First, an organic compound represented by general formula 3 below is produced by reacting bis(4-mercaptophenyl) sulfide represented by chemical formula 2 below with ω-haloalkyl alcohol, using a base as a catalyst, at 60° C. to 120° C. for four to eight hours (first process).

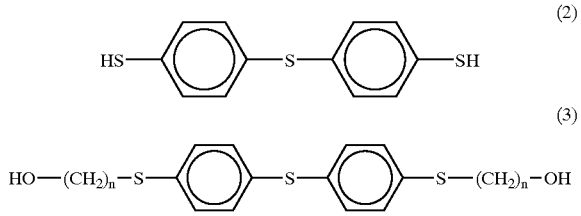

wherein n is an integer of 1 to 4.

The bis(4-mercaptophenyl) sulfide represented by chemical formula 2 is commercially available from Sumitomo Seika Chemicals Co., Ltd. under the product name of MPS.

The ω-haloalkyl alcohol used in the first process is an alcohol having a linear carbon chain with 1 to 4 carbon atoms and having a hydroxyl group at a terminal carbon of the carbon chain and halogen at the other terminal carbon of the carbon chain. More specifically, 2-chloroethanol, 3-chloro-1-propanol, 4-chloro-1-butanol, 2-bromoethanol, 3-bromo-1-propanol, 2-iodoethanol and the like can be used, for example. The number of carbon atoms of ω-haloalkyl alcohol corresponds to n of the bis(4-mercaptophenyl) sulfide derivatives of general formula 1. For example, when 2-chloroethanol is used, n in general formula 1 is 2.

As the base catalyst used in the first process, alkali metal carbonates such as $Na_2CO_3$, and $K_2CO_3$, alkaline earth metal carbonates such as $CaCO_3$ and $MgCO_3$, and alkali metal alkoxides are suitable. Among these, alkali metal carbonates are preferable. As a solvent for the base catalyst, ketones such as methyl ethyl ketone, methyl isobutyl ketone, ethers such as tetrahydrofuran and dioxane are suitable.

After the first process, the bis(4-mercaptophenyl) sulfide derivatives of general formula 1 can be produced by refluxing alkyl ester acrylate or alkyl ester methacrylate and the organic compound represented by general formula 3 in the presence of a catalyst for transesterification for 6 to 10 hours (second process).

In the second process, when alkyl ester acrylate (represented by general formula $CH_2$=CHCOOR' in which, for example, methyl groups, ethyl groups, propyl groups, butyl groups or the like can be used for R' as an alkyl group), preferably, methyl acrylate is used, bis(4-mercaptophenyl) sulfide derivatives having hydrogen as R can be obtained. Alternatively, when alkyl ester methacrylate (represented by general formula $CH_2$=C($CH_3$)COOR" in which, for example, methyl groups, ethyl groups, propyl groups, butyl groups or the like can be used for R" as an alkyl group), preferably, methyl methacrylate is used, bis(4-mercaptophenyl) sulfide derivatives having a methyl group as R can be obtained.

As the catalyst for transesterification used in the second process, alkoxy titanium such as tetrabutyl titanate, and organotin compounds such as dibutyltin oxide, dioctyltin oxide, dibutyltin diacetate, dibutyltin dilaurate are suitable. Among these, tetrabutyl titanate or dibutyltin oxide is preferable. As the amount of alkyl ester acrylate (or alkyl ester methacrylate) to be fed, 3 to 10 parts by weight per part by weight (by mass) of the organic compound of general formula 3 is preferable.

In the above-described production method, it is preferable that ω-haloalkyl alcohol is 2-haloethanol in the first process, and methyl acrylate is reacted with the compound represented by general formula 3 in the second process.

The production method of Embodiment 2 can facilitate production of the bis(4-mercaptophenyl) sulfide derivatives of general formula 1 described in Embodiment 1.

Embodiment 3

Figure 1B:
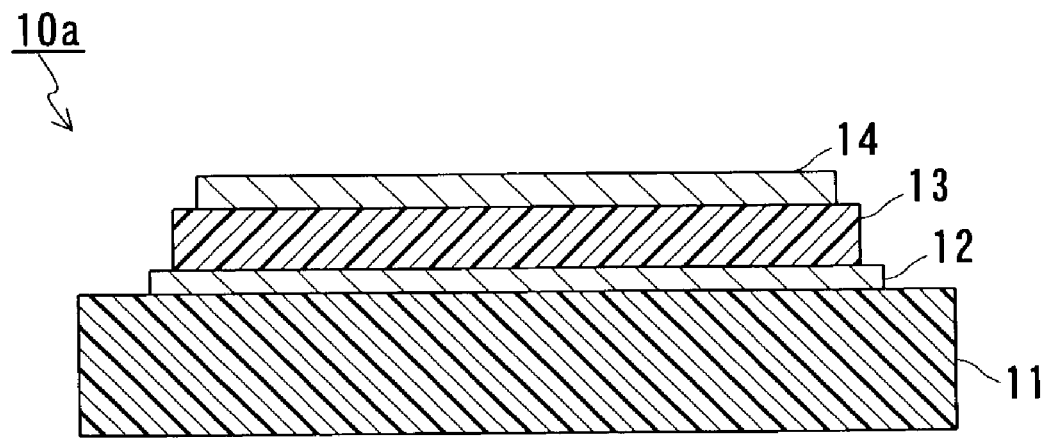
FIG. 1B is a cross-sectional view showing another example of a capacitor, which is an electronic component of the present invention.

In Embodiment 3, an example of a capacitor will be described as an electronic component of the present invention. FIG. 1A is a cross-sectional view of a capacitor 10 of Embodiment 3. The capacitor of the present invention can have a shape as shown in FIG. 1B as a capacitor 10*a*.

Referring to FIG. 1A, the capacitor 10 includes a support 11, a lower electrode film 12 formed on the support 11, a dielectric film 13 disposed mainly on the lower electrode film 12, and an upper electrode film 14 disposed mainly on the dielectric film 13. The dielectric film 13 is a resin film (an additive may further be included in the resin film). In other words, the capacitor 10 includes the dielectric film 13 and a pair of electrodes (the lower electrode film 12 and the upper electrode film 14) that are opposed with the dielectric film 13 interposed therebetween.

As the support 11, various substances can be used. More specifically, for example, films made of polymer such as polyethylene terephthalate (which may be referred to as "PET" in the following), polyethylene naphthalate (PEN), polyphenylene sulfide (PPS), polyamide (PA) or polyimide (PI) can be used. There is no limitation regarding the thickness of the support 11, but in general, a thickness of the order of 1 μm to 75 μm commonly is used. When the lower electrode film 12 also serves as the support, the support 11 is not required. The support 11 can be removed after the lower electrode film 12, the dielectric film 13 and the upper electrode film 14 are formed. In other words, the capacitor of the present invention may not be provided with the support.

For the lower electrode film 12 and the upper electrode film 14, conductive films can be used. For example, metal films can be used. More specifically, metal films containing aluminum, zinc, copper or the like as the main component can be used. There is no particular limitation regarding the thickness of the electrode films, but for example, films having a thickness of 10 nm to 150 nm can be used, and preferably, films having a thickness of 20 nm to 50 nm can be used. The lower electrode film 12 and the upper electrode film 14 of the capacitor 10 are connected to respective electric circuits. The electrode films can be connected to the electric circuits by, for example, soldering, metal spraying, clamping or the like.

The dielectric film 13 is a resin film formed by forming a thin film containing at least one type of monomer and then polymerizing the monomer in the thin film. The monomer has a molecular structure in which sulfur and an aromatic ring are covalently bonded or a molecular structure in which sulfur and an aromatic ring are bonded via an alkylene group. The thin film may contain one type of monomer or a plurality of types of monomers.

A thin film 13a (see FIG. 2B) that will be formed into the dielectric film 13 by polymerization reaction further may contain an additive, in addition to the monomer. Examples of the additive include polymerization initiators, antioxidants, plasticizers, surfactants, and adhesion improvers. As a polymerization initiator, for example, 2-benzyl-2-dimethylamino-1-(4-orpholino phenyl)-butanone-1, bis(2,4,6-trimethyl benzoyl)-phenyl phosphine oxide, 2-methyl-1[4-(methylthio)phenyl]-2-morpholino propane-1-one (which are Irgacure 369, 819 and 907, respectively, manufactured by Ciba Specialty Chemicals) can be used. As an antioxidant, for example, octadecyl-3-(3,5,-di-tert-butyl-4-hydroxyphenyl) propionate, benzene propanoic acid, 3,5-bis(1,1-dimethyl ethyl)-4-hydroxy, $C_7$ to $C_9$ side chain alkyl ester, 4,6-bis(octylthio methyl)-o-cresol (which are IRGANOX-1076,1135, and 1520L, respectively, manufactured by Ciba Specialty Chemicals) can be used.

In the case where the thin film 13a contains a polymerization initiator, the content of the polymerization initiator preferably is 0.5% by weight (% by mass) to 10% by weight, and more preferably 1% by weight to 3% by weight. When the content of the polymerization initiator is 0.5% by weight or more, the curing rate of the thin film 13a can be increased. When the content of the polymerization initiator is 10% by weight or less, the pot life of the monomer 31 (see FIG. 3) can be prevented from being too short. When the content of the polymerization initiator is 1% by weight to 3% by weight, the curing rate can be increased and the pot life of the monomer 31 can be prevented from being too short, and thus the capacitor 10 can be produced easily.

In the case where the thin film 13a contains an antioxidant, the content of the antioxidant preferably is 0.1% by weight to 10% by weight, and more preferably 0.5% by weight to 5% by weight. When the content of the antioxidant is 0.1% by weight or more, the dielectric film 13 can be prevented from being oxidized. When the content of the antioxidant is 10% by weight or less, the curing rate of the thin film 13a can be a practical value. When the content of the antioxidant is 0.5% by weight or more, the dielectric film 13 can be prevented from being oxidized remarkably. When the content of the antioxidant is 5% by weight or less, the curing rate of the thin film 13a can be a preferable value.

As the monomer contained in the thin film 13a, for example, monomers represented by general formulae 1 and 4 and chemical formulae 5 and 6 can be used.

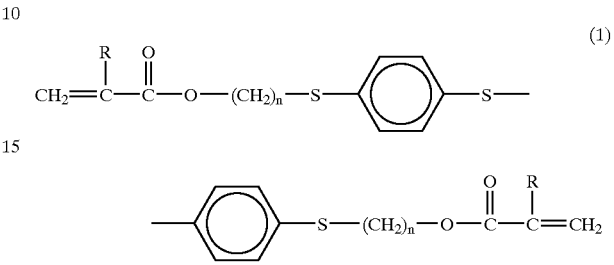

wherein R is hydrogen or a methyl group, and n is an integer of 1 to 4.

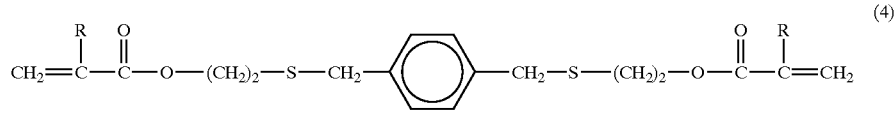

wherein R is hydrogen or a methyl group.

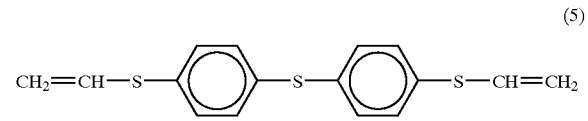

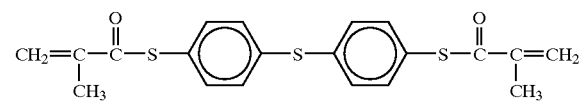

The monomers of general formula 1 can be produced by the method described in Embodiment 2. The monomers of general formula 4 can be produced by a method as described below. The monomers of chemical formulae 5 and 6 are commercially available from Sumitomo Seika Chemicals under the products names of MPV and MPSMA, respectively.

For the monomers of general formula 1, it is especially preferable that R is hydrogen and n is 2. The thin film 13a can contain the monomers of general formulae 1 and 4 and chemical formulae 5 and 6 in an arbitrary ratio, and for example, can contain the monomer of general formula 1 in a ratio of 50% by weight or more and further contain the monomer of general formula 4.

Hereinafter, a method for producing the monomers of general formula 4 will be described. First, an intermediate product represented by chemical formula 7 below is produced by reacting p-xylene dichloride with 2-mercaptoethanol in the same manner as in the first process for producing the monomers of general formula 1.

(7)

Thereafter, this intermediate product is reacted with methyl acrylate or methyl methacrylate in the same manner as in the second process for producing the monomers of general formula 1, and thus the monomer of general formula 4 can be synthesized easily.

Next, a method for producing the capacitor 10 will be described. FIGS. 2A to 2D show an example of the production process.

Figure 2A:
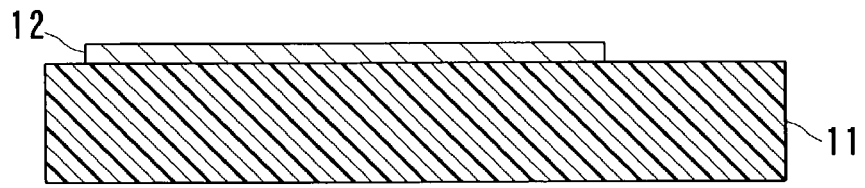
FIGS. 2A to 2D are process drawings showing an example of a method for producing a capacitor, which is an electronic component of the present invention.

Referring to FIG. 2A, first, the lower electrode film 12 is formed on the support 11. The lower electrode film 12 can be formed by vacuum evaporation such as electron beam evaporation, resistance heating evaporation, and induction heating evaporation, ion plating, sputtering, plating or the like. In order to form the lower electrode film 12 into a predetermined shape, a metal mask can be used, or photolithography, etching or other techniques can be used.

Figure 2B:
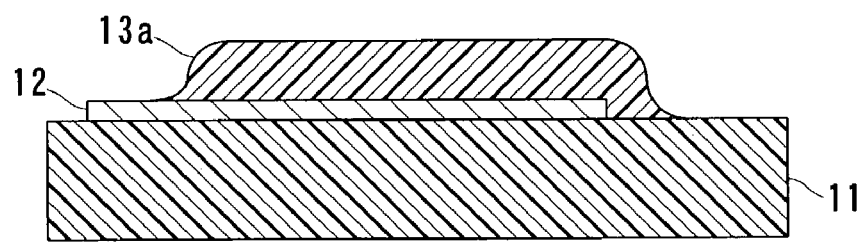
Figure 3:
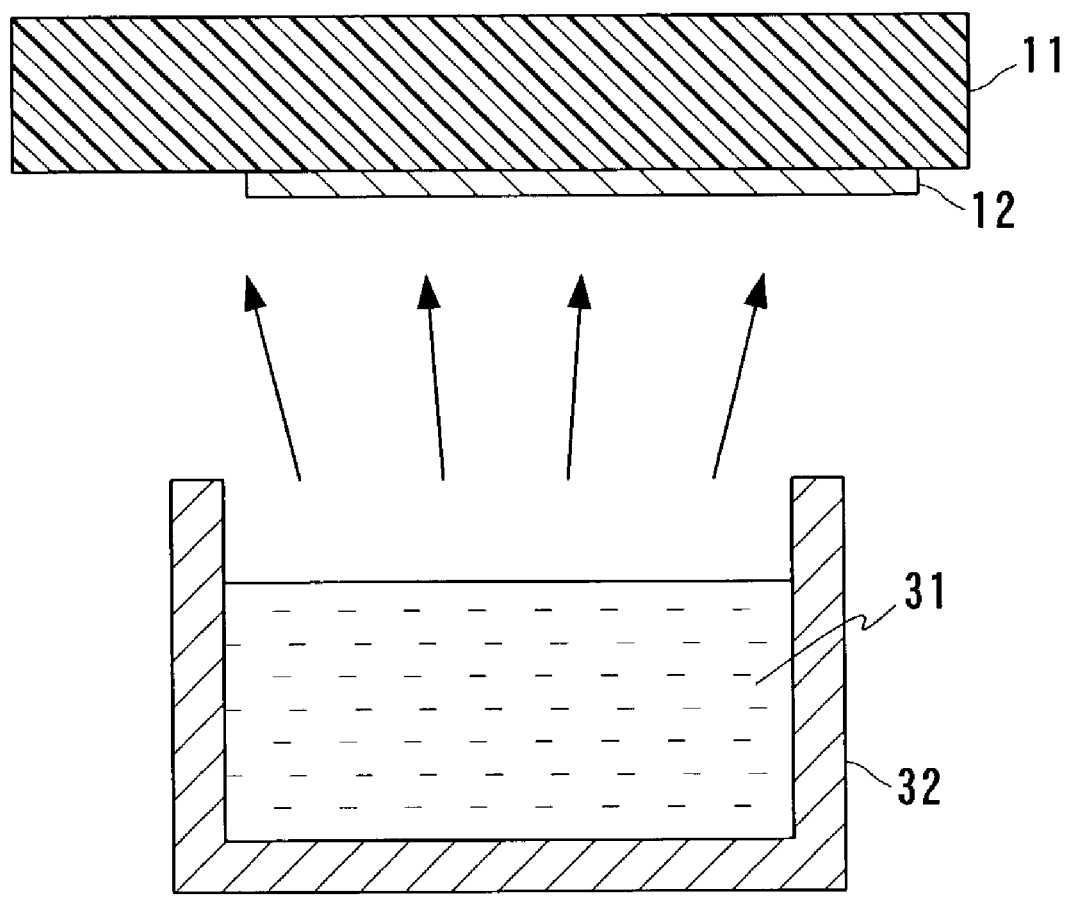
FIG. 3 is a drawing showing one step of the production process shown in FIG. 2.

Next, as shown in FIG. 2B, the thin film 13a containing a monomer is formed on the lower electrode film 12. The thin film 13a is a film that will be formed into the dielectric film 13 by a polymerization reaction, and contains the above-described monomers represented by general formulae 1 and 4 and chemical formulae 5 and 6 and additives. The thin film 13a can be formed by placing a container 32 containing a monomer 31 for forming the thin film 13a under a vacuum such that the container 32 faces the lower electrode film 12, as shown in FIG. 3, and heating the container 32 to evaporate the monomer. A metal mask (not shown) can be used to form the thin film 13a into a predetermined shape.

Figure 2C:
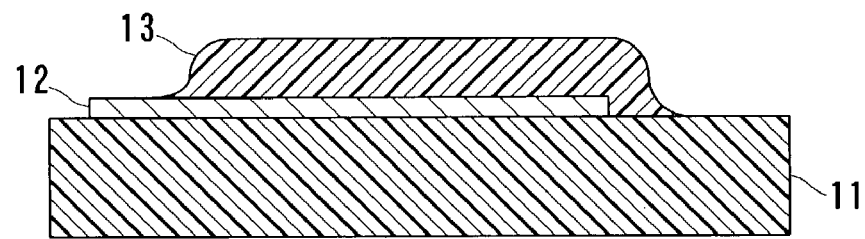

Then, a polymerization reaction of the monomer is caused in the thin film 13a, and thus the dielectric film 13 is formed, as shown in FIG. 2C. The polymerization reaction (curing) can be caused by, for example, irradiating the thin film 13a with ultraviolet rays or electron beams.

Figure 2D:
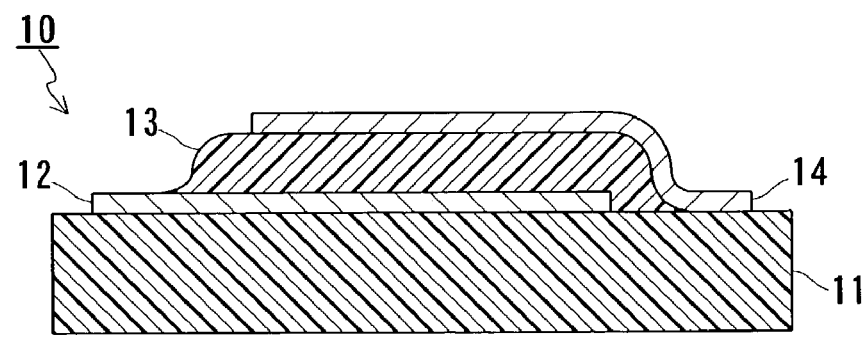

Next, as shown in FIG. 2D, the upper electrode film 14 may be formed in the same manner as the lower electrode film 12 is formed. Thus, the capacitor 10 can be produced. The capacitor 10a can be produced by the same production method.

In the capacitor of Embodiment 3, the dielectric film 13 hardly is changed in its properties even under high humidity or high temperature, and thus a capacitor having excellent characteristics even under high humidity and high temperature can be obtained.

Embodiment 4

Figure 4A:
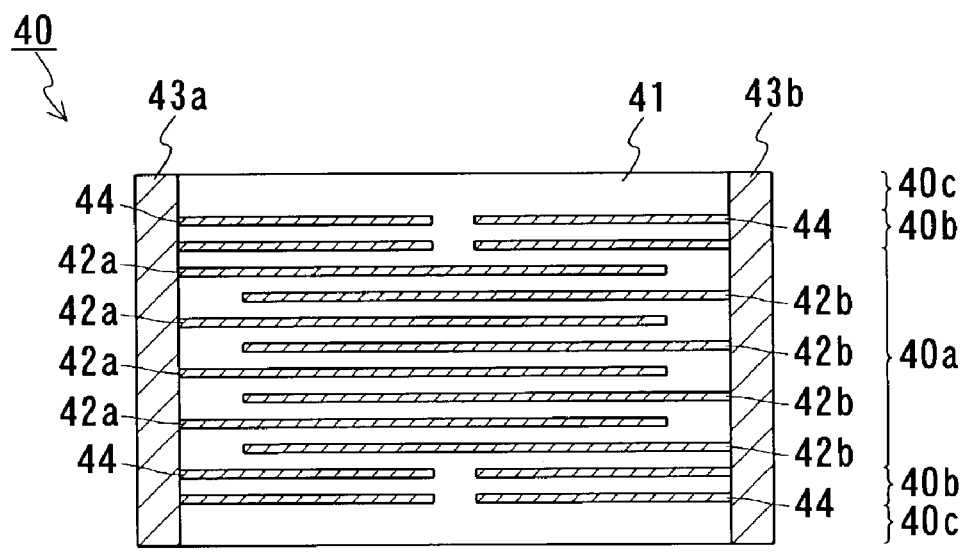
FIG. 4A is a cross-sectional view showing yet another example of a capacitor, which is an electronic component of the present invention.
Figure 4B:
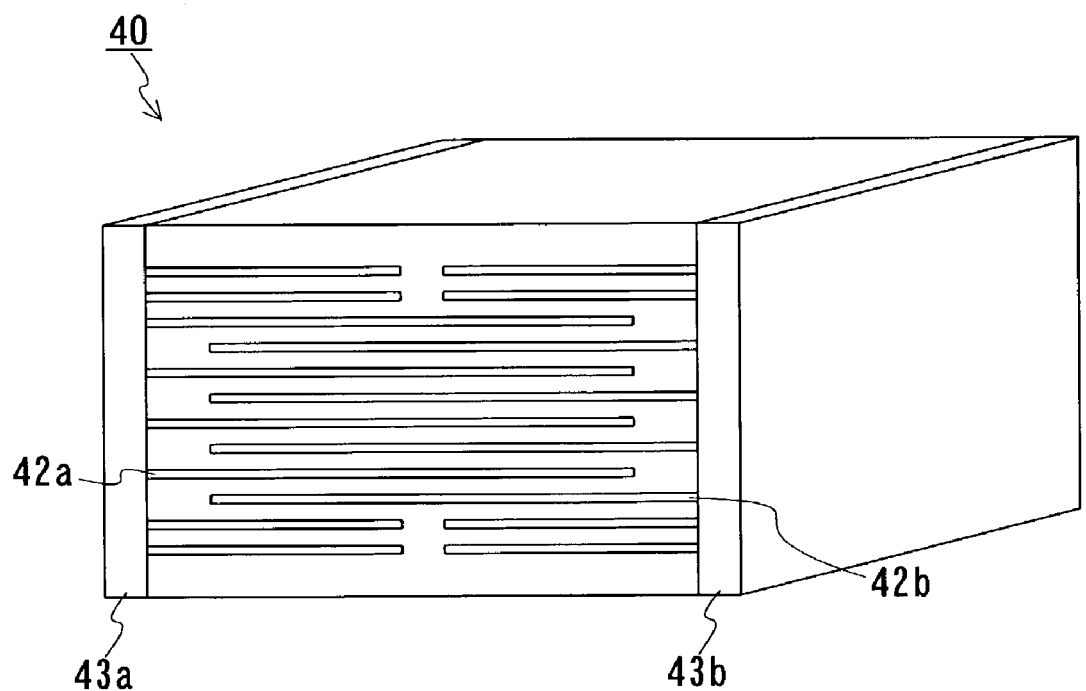
FIG. 4B is a perspective view of FIG. 4A.

In Embodiment 4, another example of a capacitor will be described as an electronic component of the present invention. FIG. 4A is a cross-sectional view of a capacitor 40 of Embodiment 4, and FIG. 4B is a perspective view thereof. The same aspects as described in Embodiment 3 will not be described further.

Referring to FIGS. 4A and 4B, the capacitor 40 includes a dielectric film 41 (hatching is omitted), a plurality of electrodes 42a disposed in the dielectric film 41, electrodes 42b opposed to the electrodes 42a, and external electrodes 43a and 43b connected to the electrodes 42a and 42b, respectively. In other words, the capacitor 40 includes at least one pair of electrodes opposed to each other with at least a part of the dielectric film 41 interposed therebetween. The capacitor 40 further includes metal thin films 44 disposed on the outer sides of the electrodes 42a and 42b. The portion of the capacitor 40 in which the plurality of electrodes 42a and the electrodes 42b opposed to the electrodes 42a are present serves as an element layer 40a. The portions of the capacitor 40 in which the metal thin films 44 are formed serve as reinforcing layers 40b. The portions of the capacitor 40 that are constituted only by the dielectric film 41 serve as protective layers 40c. The reinforcing layers 40b and the protective layers 40c are layers for preventing the element layer 40a from being damaged by thermal load or external force. It is possible that the reinforcing layers 40b or the protective layers 40c are not provided in the capacitor 40.

The dielectric film 41 is the same film as the dielectric film 13 described in Embodiment 3 and can be produced by the same method as above.

The capacitor 40 can be produced by the method described in Embodiment 3. However, the method for producing the capacitor 40 is different from the method described in Embodiment 3 in that it is necessary to laminate the dielectric films and the electrodes 42a or 42b alternately and to form the external electrodes 43a and 43b in the method for producing the capacitor 40. The external electrodes 43a and 43b can be formed by, for example, performing metal spraying, forming bump electrodes, applying conductive paste or other techniques.

In the capacitor 40 of Embodiment 4, the dielectric film 41 hardly is changed in its properties even under high humidity or high temperature, and thus a capacitor having excellent characteristics even under high humidity or high temperature can be obtained.

EXAMPLES

Hereinafter, the present invention will be described more specifically by way of examples.

Example 1

In Example 1, an example of the production of a monomer that is a bis(4-mercaptophenyl) sulfide derivative represented by general formula 1 and has hydrogen as R and 2 as n will be described. Also, an example of the production of a monomer that is a bis(4-mercaptophenyl) sulfide derivative represented by general formula 1 and has a methyl group as R and 4 as n will be described.

First, 25.0 g (0.10 moles) of the bis(4-mercaptophenyl) sulfide represented by chemical formula 2, 16.1 g (0.20 moles) of 2-chloroethanol, 27.6 g (0.20 moles) of potassium carbonate, and 300 ml of methyl isobutyl ketone were placed in a flask with a volume of 1 liter and reacted by continuous stirring under reflux for 6 hours. After completion of the reaction, 50 ml of a 5% hydrochloric acid solution was added gradually to the obtained solution under stirring. Thereafter, 300 ml of toluene was added thereto. The thus obtained solution was washed with distilled water repeatedly until the pH reached 7. Then, the washed solution was dried with anhydrous sodium sulfate, and the solvent was removed by distillation. Thus, the intermediate product represented by chemical formula 8 below was obtained in an amount of 32 g.

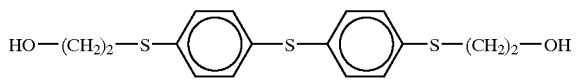
(8)

Then, 320 g of methyl acrylate, 0.32 g of tetrabutyl titanate (1/100 parts by weight with respect to the intermediate product), and 0.16 g of p-methoxyphenol (5/1000 parts by weight with respect to the intermediate product) as a polymerization inhibitor were added to 32 g of the intermediate product represented by chemical formula 8, followed by 10 hour reflux, and then methyl acrylate was removed by distillation. The thus obtained reaction product was dissolved in 300 ml of toluene, and then this solution was washed sequentially, first with 50 ml of a 5% sodium hydroxide solution and then with 50 ml of a 5% hydrochloric acid solution. Further, the solution was washed with distilled water until the pH reached 7, and then dried with anhydrous sodium sulfate. To this solution, 0.16 g of p-methoxyphenol was added, and thereafter, the solvent was removed by distillation. Thus, a semi-solid having a melting point of 20° C. was obtained. This semi-solid was measured by infrared spectroscopic analysis and gel permeation chromatography (GPC).

Figure 5:
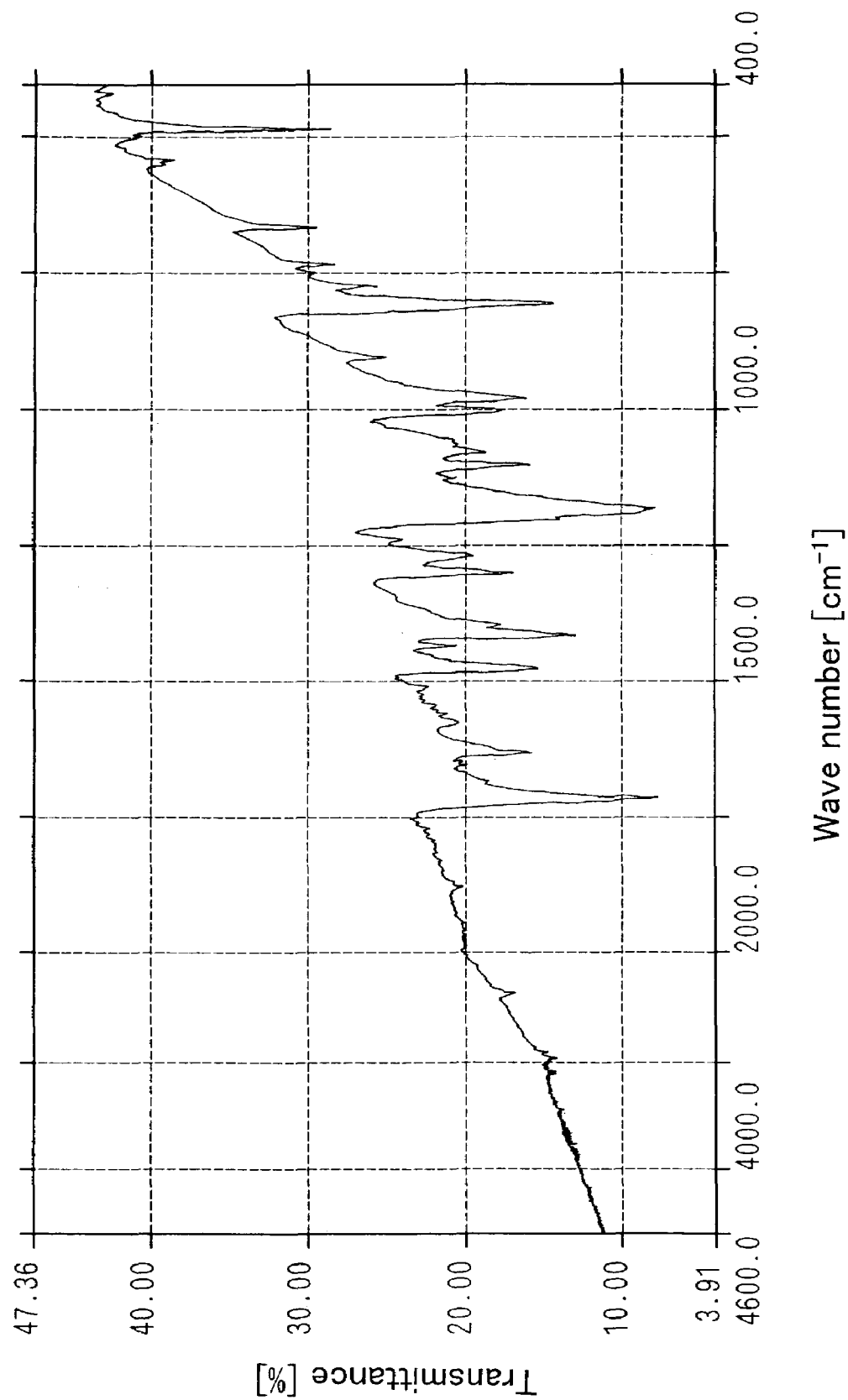
FIG. 5 is a graph showing the IR spectrum of bis(4-acryloyl oxyethylene thiophenyl) sulfide, which is an example of a monomer of the present invention used for the production of electronic components.

FIG. 5 shows the results of measurement by infrared spectroscopic analysis. As seen from FIG. 5, an absorption peak at 1725 cm$^{-1}$ based on ester acrylate was observed. In GPC, the raw material, the intermediate product and byproducts were not detected. From the aspects described above, the finally obtained semi-solid turned out to be bis(4-acryloyloxyethylene thiophenyl) sulfide represented by chemical formula 9 below.

Example 2

In Example 2, an example of production of a monomer that is represented by general formula 4 and has a methyl group as R will be described.

First, 17.5 g (0.10 moles) of p-xylene dichloride, 15.6 g (0.20 moles) of 2-mercaptoethanol, 27.6 g (0.20 moles) of potassium carbonate, and 300 ml of methyl isobutyl ketone were placed in a flask with an volume of 1 liter and reacted by continuous stirring under reflux for 6 hours. After completion of the reaction, the obtained solution was treated in the same manner as in Example 1, and thus, the intermediate product represented by chemical formula 7 below was obtained in an amount of 23 g.

(7)

Then, 230 g of methyl acrylate, 0.23 g of tetrabutyl titanate (1/100 parts by weight with respect to the intermediate product), and 0.12 g of p-methoxyphenol (5/1000 parts by weight with respect to the intermediate product) as a polymerization inhibitor were added to 23 g of the intermediate product represented by chemical formula 7, followed by 10 hour reflux, and methyl methacrylate was removed by distillation. The thus obtained reaction product was treated

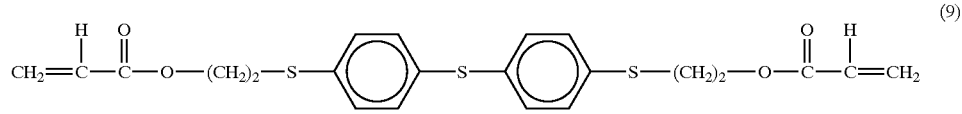
(9)

Next, an example of production of bis(4-methacryloyloxybutylene thiophenyl) sulfide that is an organic compound represented by general formula 1 and has a methyl group as R and 4 as n will be described.

In this case, the same method as that for producing the bis(4-acryloyloxyethylene thiophenyl) sulfide represented by chemical formula 9 can be used except that a different raw material is used. More specifically, 2-chloroethanol was replaced by 4-chloro-1-butanol, and methyl acrylate was replaced by methyl methacrylate. Thus, bis(4-methacryloyloxy butylene thiophenyl) sulfide represented by chemical formula 10 was obtained.

in the same manner as in Example 1, and thus, a transparent light yellow liquid was obtained. This liquid was measured by infrared spectroscopic analysis and GPC.

Figure 6:
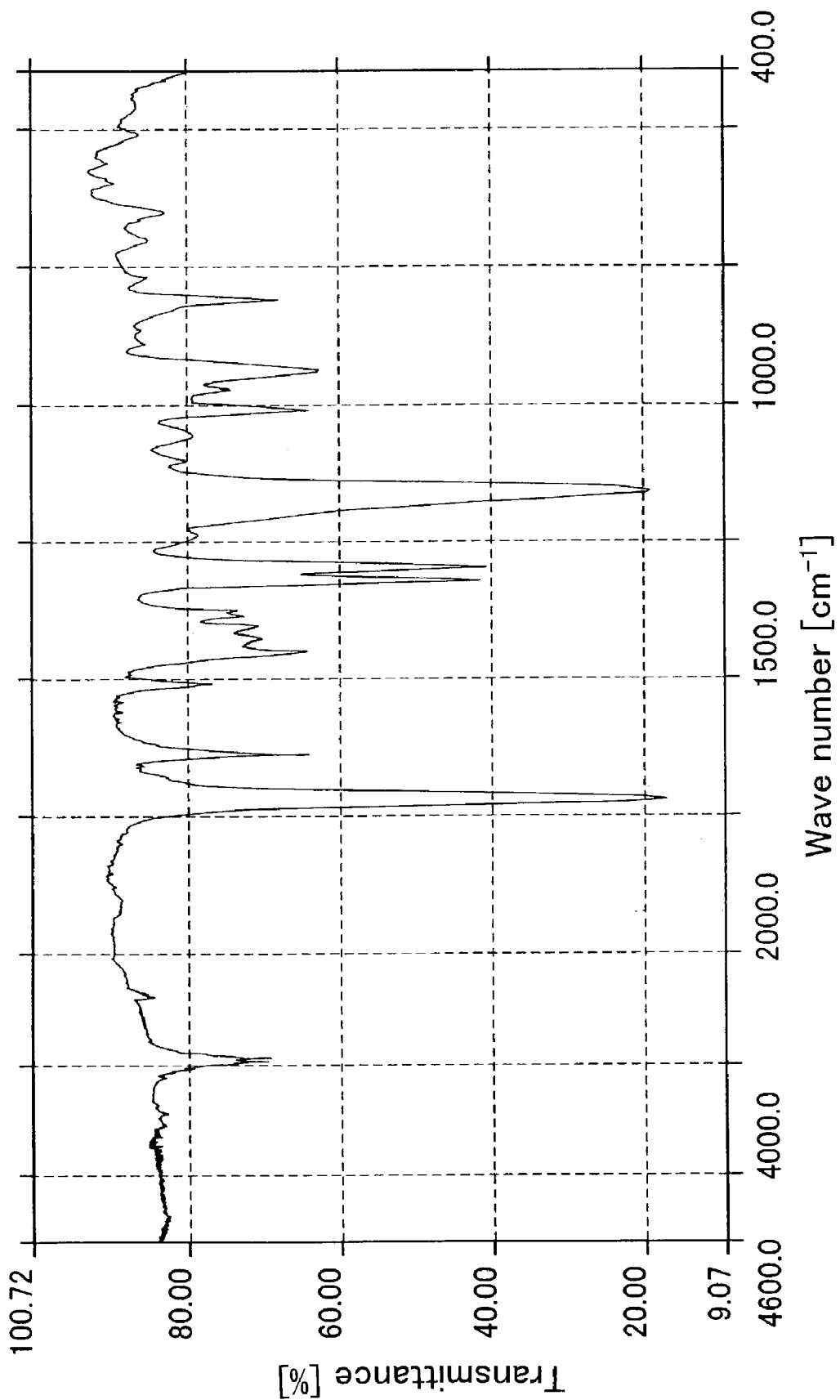
FIG. 6 is a graph showing the IR spectrum of 1,4-bis (methacryloyl oxyethylene thiomethyl) benzene, which is an example of a monomer of the present invention used for production of electronic components.

FIG. 6 shows the results of measurement by infrared spectroscopic analysis. As seen from FIG. 6, an absorption peak at 1725 cm$^{-1}$ based on ester methacrylate was observed. In GPC, the raw material, the intermediate product and byproducts were not detected. From the aspects described above, the finally obtained liquid turned out to be 1,4-bis(methacryloyloxyethylene thiomethyl) benzene represented by chemical formula 11 below.

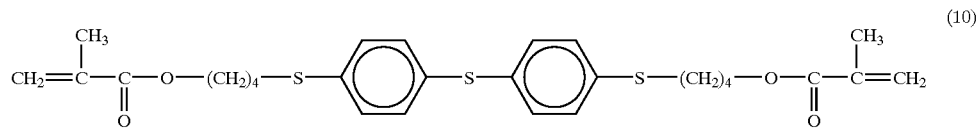
(10)

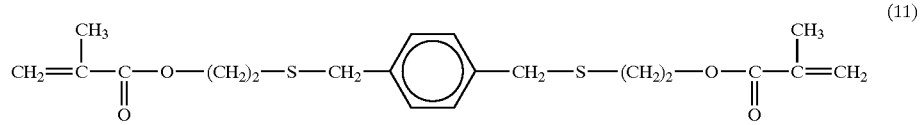

(11)

The monomer of general formula 1 having hydrogen as R can be produced by the same method as the above-described method except that methyl acrylate, instead of methyl methacrylate, is reacted to the intermediate product represented by chemical formula 7.

Example 3

In Example 3, an example of production of the capacitor shown in FIG. 1A as an electronic component of the present invention will be described with reference to FIGS. 2A to 2D.

First, a PET substrate 11 having a thickness of 25 μm was prepared, and the lower electrode film 12 (30 nm thick) made of aluminum was deposited on the PET substrate 11 by evaporation at a deposition rate of 100 nm/sec. (see FIG. 2A).

Thereafter, the thin film 13a (200 nm thick) made of the monomer was formed on the lower electrode film 12 by evaporating the monomer (see FIG. 2B). More specifically, the container 32 containing the monomer 31, as shown in FIG. 3, was heated such that the deposition rate became 500 nm/sec., and the thin film 13a was formed such that a part of the lower electrode film 12 was exposed.

Thereafter, the thin film was irradiated with accelerated electrons at −15 kV at a density of 50 μA/cm² for 2 seconds to polymerize the monomer in the thin film, and thus the dielectric film 13 was formed (see FIG. 2C).

Thereafter, the upper electrode film 14 made of aluminum was formed in a position that is above the dielectric film 13 and is not in contact with the lower electrode film 12 by evaporation at a deposition rate of 100 nm/sec. (see FIG. 2D).

In Example 3, 5 different capacitors were produced, using the monomer of chemical formula 9, the monomer of chemical formula 11, the monomer of chemical formula 11 containing 3% by weight of IRGANOX 1520L as an antioxidant, the monomer of chemical formula 5, and the monomer of chemical formula 6. Thus, working samples 1 to 5 were obtained.

Furthermore, as comparative examples, two types of capacitors (comparative samples 1 and 2) were produced, using monomers represented by chemical formulae A and B.

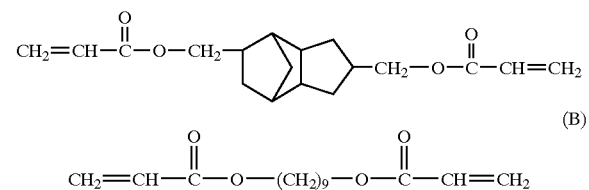

Regarding the above-described 7 types of capacitors, (i) a moisture absorption capacitance change ratio and (ii) a high temperature load capacitance change ratio were measured. For the capacitors produced with the monomers of chemical formulae 9, A and B, the changes in the thickness when the capacitors were immersed in hot water were examined. The method for evaluation will be described later. Table 1 shows the evaluation results.

TABLE 1

| | Monomer | Antioxidant | Moisture absorption capacitance change ratio (%) | High temperature load capacitance change ratio | Thickness change |
|---|---|---|---|---|---|
| Working sample 1 | chemical formula 9 | Not added | +5.5 | −1% to 0% | No change |
| Working sample 2 | chemical formula 11 | Not added | +7.0 | −2% | — |
| Working sample 3 | chemical formula 11 | 3% by mass | +7.0 | −1% to 0% | — |
| Working sample 4 | chemical formula 5 | Not added | +1.0 | −1% to 0% | — |
| Working sample 5 | chemical formula 6 | Not added | +6.4 | −1% to 0% | — |
| Com. Sample 1 | chemical formula A | Not added | +18 | −5% | 200% to 300% |
| Com. Sample 2 | chemical formula B | Not added | +8.0 | ≦−10% | 200% to 300% |

As seen from Table 1, the capacitors of working samples 1 to 5 exhibited better characteristics than those of the capacitors of comparative samples 1 and 2 in the evaluation of both the moisture absorption capacitance change ratio and the high temperature load capacitance change ratio. More specifically, capacitors having excellent characteristics even under high humidity and high temperature were obtained by forming dielectric films of the capacitors with the monomers of the present invention having a molecular structure in which sulfur and an aromatic ring are covalently bonded or a molecular structure in which sulfur and an aromatic ring are bonded via an alkylene group.

Hereinafter, the method for evaluating the characteristics shown in Table 1 will be described in detail.

(i) The moisture absorption capacitance change ratio was evaluated in the following manner. First, a capacitor was dried in a 105° C. atmosphere for 10 hours, and the initial capacitance $C_{11}$ was measured. The capacitance was measured while a sine wave with a frequency of 1 kHz and a voltage of 1 Vrms was applied to the capacitor. Thereafter, the capacitor was stored in an atmosphere at a temperature of 60° C. and a relative humidity of 95% for 100 hours. Then, the capacitance $C_{12}$ after the storage (the capacitance when the capacitor absorbed moisture) was measured under the same conditions as the initial capacitance was measured. The moisture absorption capacitance change ratio is a value represented by $(C_{12}-C_{11})/C_{11} \times 100$ (%). The smaller the moisture absorption capacitance change ratio is, the higher the capacitance stability in a humid atmosphere is, and such capacitors having a small change ratio are preferable as a product. Therefore, it is particularly important that the moisture absorption capacitance change ratio is as small as possible.

(ii) The high temperature load capacitance change ratio was evaluated in the following manner. First, a capacitor was dried in a 105° C. atmosphere for 10 hours, and the initial capacitance $C_{21}$ was measured. The capacitance was measured while a sine wave with a frequency of 1 kHz and a voltage of 1 Vrms was applied to the capacitor. Thereafter, the capacitor was stored for 50000 hours in an atmosphere at a temperature of 105° C. while a dc voltage of 16V was applied. Then, the capacitance $C_{22}$ after the storage was measured under the same conditions as the initial capacitance was measured. The high temperature load capacitance change ratio is a value represented by $(C_{22}-C_{21})/C_{21} \times 100$ (%). A capacitor having a smaller absolute value of the high temperature load capacitance change ratio is less likely to be oxidized at high temperatures, and such a capacitor is preferable as a product. In particular, in recent years, the high temperature resistance of electronic components has become important, as CPUs are operated at a high speed. Therefore, the smallness of the absolute value of the high temperature load capacitance change ratio is an important indication when evaluating capacitors.

(iii) The change in the thickness when capacitors were immersed in hot water was evaluated in the following manner. First, the thickness of a capacitor was measured. Then, the capacitor was immersed in hot water at 90° C. for 3.5 hours. Thereafter, the capacitor was taken out of the hot water and the thickness was measured again. Then, the thicknesses before and after immersion in hot water were compared. The larger the change in the thickness is, the more moisture the dielectric film absorbs, and the adhesion between the dielectric film and the electrode film made of metal is degraded. Therefore, a capacitor having a smaller change in the thickness has a higher adhesion between the dielectric film and the electrode film, so that such a capacitor is preferable as a product.

Furthermore, the dielectric loss tangent (tan δ) was evaluated with respect to each sample, and the results were such that the capacitors of working samples 1 to 5 exhibited characteristics equal to those of comparative samples 1 and 2 or even better characteristics. The dielectric loss tangent (tan δ) was measured while a sine wave with a frequency of 1 kHz and a voltage of 1 Vrms was applied to the capacitor. The smaller the dielectric loss tangent is, the smaller the power consumed by the capacitor itself is, so that such a capacitor having a smaller dielectric loss tangent is preferable as a product.

In the above-described embodiments and examples, the case where the electronic component of the present invention is a capacitor have been described. However, the electronic component of the present invention is not limited thereto, and any electronic components can be used, as long as the dielectric film described in the above embodiments is provided. More specifically, for example, the present invention can be used for coils, resistors, capacitive cells, support members of other electronic components or the like.

The embodiments of the present invention have been described above by way of examples. However, the present invention is not limited to the above-described embodiments and can be applied to other embodiments based on the technical idea of the present invention.

INDUSTRIAL APPLICABILITY

As described above, the present invention provides novel bis(4-mercaptophenyl) sulfide derivatives represented by general formula 1. The bis(4-mercaptophenyl) sulfide derivatives represented by general formula 1 of the present invention are useful for electronic components, such as capacitors, coils, resistors, capacitive cells, support members of other electronic components or the like. When a dielectric film is formed using the bis(4-mercaptophenyl) sulfide derivatives and is used in an electronic component, the electronic component can have excellent characteristics even under high humidity and high temperature.

Moreover, the method of the present invention for producing bis(4-mercaptophenyl) sulfide derivatives makes it possible to produce the bis(4-mercaptophenyl) sulfide derivatives represented by general formula 1 easily.

Moreover, according to the electronic component of the present invention, an electronic component having excellent characteristics even under high humidity and high temperature can be obtained. In particular, a high quality capacitor with reduced changes in the characteristics due to the environment can be obtained by applying the present invention to a capacitor.

The invention claimed is:

1. A capacitor comprising:
   a dielectric film, and
   a pair of electrodes including a lower electrode and an upper electrode, wherein the upper electrode and lower electrode are opposed to each other with at least a part of the dielectric film interposed therebetween and the upper electrode is formed in a position that is not in contact with the lower electrode,
   wherein the dielectric film is formed by applying a thin film containing a monomer of general formula (1) to a surface of the lower electrode and polymerizing the monomer,

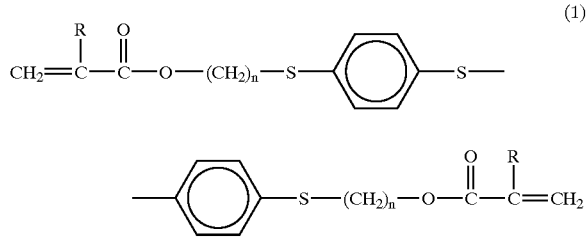

wherein R is hydrogen or a methyl group, and n is an integer of 1 to 4.

2. The capacitor according to claim 1, wherein the thin film further comprises an additive.

3. The capacitor according to claim 2, wherein the additive comprises an antioxidant.

4. The capacitor according to claim 2, wherein the additive comprises a polymerization initiator.

5. A capacitor comprising:
   a dielectric film, and
   a pair of electrodes, including a lower electrode and an upper electrode, wherein the upper electrode and lower electrode are opposed to each other with at least a part of the dielectric film interposed therebetween and the upper electrode is formed in a position that is not in contact with the lower electrode,
   wherein the dielectric film is formed by applying a thin film containing a monomer of general formula (4) to a surface of the lower electrode and polymerizing the monomer,

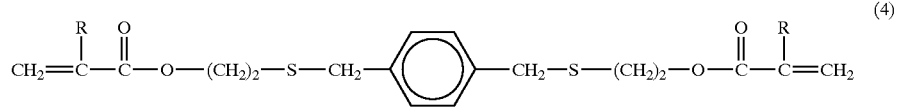

(4)

wherein R is hydrogen or a methyl group.

6. The capacitor according to claim 5, wherein the thin film further comprises an additive.

7. The capacitor according to claim 6, wherein the additive comprises an antioxidant.

8. The capacitor according to claim 6, wherein the additive comprises a polymerization initiator.

9. A capacitor comprising:
a dielectric film, and
a pair of electrodes, including a lower electrode and an upper electrode, wherein the upper electrode and lower electrode are opposed to each other with at least a part of the dielectric film interposed therebetween and the upper electrode is formed in a position that is not in contact with the lower electrode,
wherein the dielectric film is formed by applying a thin film containing a monomer of general formula (5) to a surface of the lower electrode and polymerizing the monomer

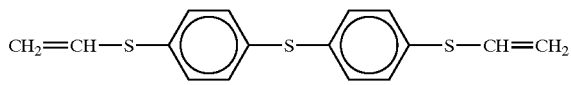

(5)

10. The capacitor according to claim 9, wherein the thin film further comprises an additive.

11. The capacitor according to claim 10, wherein the additive comprises an antioxidant.

12. The capacitor according to claim 10, wherein the additive comprises a polymerization initiator.

13. A capacitor comprising:
a dielectric film; and
a pair of electrodes, including a lower electrode and an upper electrode, wherein the upper electrode and lower electrode are opposed to each other with at least a part of the dielectric film interposed therebetween and the upper electrode is formed in a position that is not in contact with the lower electrode,
wherein the dielectric film is formed by applying a thin film containing a monomer of general formula (6) to a surface of the lower electrode and polymerizing the monomer

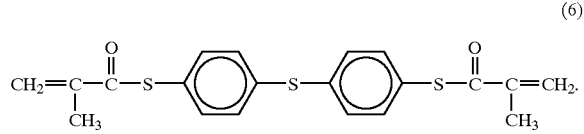

(6)

14. The capacitor according to claim 13, wherein the thin film further comprises an additive.

15. The capacitor according to claim 14, wherein the additive comprises an antioxidant.

16. The capacitor according to claim 14, wherein the additive comprises a polymerization initiator.

* * * * *